(12) United States Patent
Shimp et al.

(10) Patent No.: US 9,511,170 B2
(45) Date of Patent: Dec. 6, 2016

(54) GLASSY CALCIUM PHOSPHATE PARTICULATES, COATINGS AND RELATED BONE GRAFT MATERIALS

(75) Inventors: Lawrence A. Shimp, Morganville, NJ (US); William G. Hubbard, Burlington, WI (US); Keith A. Orlowski, Muskego, WI (US)

(73) Assignee: CaP Biomaterials, LLC, East Troy, WI (US)

( * ) Notice: Subject to any disclaimer, the term of this patent is extended or adjusted under 35 U.S.C. 154(b) by 0 days.

(21) Appl. No.: 13/134,241

(22) Filed: Jun. 2, 2011

(65) Prior Publication Data

US 2011/0300188 A1  Dec. 8, 2011

Related U.S. Application Data

(60) Provisional application No. 61/350,639, filed on Jun. 2, 2010.

(51) Int. Cl.

| A61K 33/42 | (2006.01) |
|---|---|
| A61P 19/08 | (2006.01) |
| A61K 9/14 | (2006.01) |
| A61L 27/30 | (2006.01) |
| A61L 27/32 | (2006.01) |
| A61L 27/50 | (2006.01) |
| A61L 27/54 | (2006.01) |
| A61K 9/00 | (2006.01) |

(52) U.S. Cl.
CPC .............. *A61L 27/30* (2013.01); *A61L 27/32* (2013.01); *A61L 27/50* (2013.01); *A61L 27/54* (2013.01); *C23C 4/11* (2016.01); *A61K 9/0024* (2013.01); *A61L 2300/606* (2013.01); *A61L 2430/02* (2013.01)

(58) Field of Classification Search
None
See application file for complete search history.

(56) References Cited

U.S. PATENT DOCUMENTS

| 4,223,412 | A | * | 9/1980 | Aoyagi et al. ............... 623/23.6 |
|---|---|---|---|---|
| 5,074,916 | A | * | 12/1991 | Hench et al. .................... 106/35 |
| 5,147,829 | A | | 9/1992 | Hench et al. |
| 6,221,111 | B1 | | 4/2001 | Piveteau et al. |
| 6,582,763 | B1 | * | 6/2003 | Nishimura et al. ........... 427/216 |
| 6,846,853 | B2 | | 1/2005 | Shimp |
| 2001/0031799 | A1 | * | 10/2001 | Shimp .......................... 523/105 |
| 2006/0199024 | A1 | | 9/2006 | Lima et al. |
| 2006/0199876 | A1 | * | 9/2006 | Troczynski ............. A61L 27/32 523/115 |
| 2008/0221681 | A1 | * | 9/2008 | Trieu et al. ................. 623/11.11 |

FOREIGN PATENT DOCUMENTS

| CN | 101554491 A | 10/2009 |
|---|---|---|
| JP | 04038959 | 2/1992 |
| JP | 2002210002 | 7/2002 |
| WO | 9610985 | 4/1996 |

OTHER PUBLICATIONS

Sandeep et al., Characterization of Novel Bioactive Glass Coated Hydroxyapatite Granules inn Correlation with in vitro and in vivo Studies, Trends Biomater. Artif. Organs, 19 (2006) 99-107.*
Nair et al., Cell Interaction Studies with Novel Bioglass Coated Hydroxyapatite Porous Blocks, Trends Bioimater. Artif. Organs, vol. 19 (2006) 108-114.*
Bernnhardt et al., In vitro characterization of bone cell activity on triphasic ceramic composites from calcium silicate, beta-tricalcium, J. Clin Rehab. Tiss. Eng. Res., 14 (2010) 3033-3040.*
Borum et al., Surface modification of hydroxyapatite. Part II. Silica, Biomaterials 24 (2003) 3681-3688.*
Arinzeh et al., A comparative study of biphasic calcium phosphate ceramics for human mesenchymal stem-cell-induced bone formation, Biomaterials 26 (2005) 3631-3638.*
Sandeep et al., Characterization of Novel Bioactive Glass Coated Hydroxyapatite Granules inn Correlation with in vitro and in vivo Studies, Trends Biomater. Artif. Organs, 19 (2006) 99-107 (Sandeep).*
Borum et al., Surface modification of hydroxyapatite. Part II. Silica, Biomaterials 24 (2003) 3681-3688 (Borum).*
Arinzeh et al., A comparative study of biphasic calcium phosphate ceramics for human mesenchymal stem-cell-induced bone formation, Biomaterials 26 (2005) 3631-3638 (Arinzeh).*
PCT Search Report from PCT/US2011/001001 issued Feb. 24, 2012.
Extended European Search Report for European Application No. 11790111.6 dated Apr. 28, 2016, 11 pages.

* cited by examiner

*Primary Examiner* — Bethany Barham
*Assistant Examiner* — Dominic Lazaro
(74) *Attorney, Agent, or Firm* — Reinhart Boerner Van Deuren s.c.

(57) ABSTRACT

Calcium phosphate and related coating powder particles comprising a surface component comprising a silicate content, plasma sprayed coatings thereof on implantable medical/dental devices, and bone grafting materials of such coated particles. Optionally, biologically active agents such as bone morphogenetic proteins, growth factors, analgesics, and antibiotics can be incorporated therein.

7 Claims, No Drawings

GLASSY CALCIUM PHOSPHATE PARTICULATES, COATINGS AND RELATED BONE GRAFT MATERIALS

This application claims priority benefit from application serial No. 61/350,639, filed Jun. 2, 2010, the entirety of which is incorporated herein by reference.

BACKGROUND OF THE INVENTION

Calcium hydroxyapatite (HA) plasma sprayed coatings are widely used for implantable device coatings. Basically, such a process entails coating powder particles passed through a plasma flame where surface melting (at least) occurs, enabling the particles to stick to a device surface and to each other. However, HA is difficult to melt; indeed, it has no melt phase and melts only with decomposition. Controlling the coating process to provide sufficient melting for coating adhesion and formation without excessive decomposition of the HA powder is difficult. Further, mechanical forces and abrasion during surgical implantation can damage an HA coating.

After implantation, such a coating helps to accelerate bone formation around the implant device. In difficult sites, such as where there is mechanical movement or because of poor implant stability, bone integration may not occur: The result can be fibrous tissue encapsulation. Bone formation may also not be successful in patients with certain medical problems that inhibit healing such as diabetes, or in patients who are smokers, have poor nutrition, or have bone that has been compromised by radiation treatments, for example. While standard coatings do well in most cases, they can be inadequate in such marginal applications, and a more bioactive coating would be advantageous.

As summarized, such coatings have several well-recognized deficiencies. Problems relate to production, substrate bonding strength, bonding strength within the coating, and the speed of tissue integration. As a result, there remains an on-going search in the art for improved calcium phosphate coatings and particulate precursors.

SUMMARY OF THE INVENTION

In light of the foregoing, it is an object of the present invention to provide calcium phosphate compositions with incorporated biocompatible glass components for use as surface coating powders or bone graft materials, and methods for the preparation, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to provide a coating particulate component with a melt phase without calcium phosphate decomposition.

It can also be an object of the present invention to enhance coating strength and/or substrate adhesion.

It can also be an object of the present invention to provide such calcium phosphate compositions with a silicate glass component, optionally without use of thermal spraying techniques.

It can also be an object of the present invention, alone or in conjunction with any one or more of the preceding objectives, to improve biological activity of such calcium phosphate particulates, resultant coating compositions and/or related bone grafting materials.

Other objects, features, benefits and advantages of the present invention will be apparent from this summary and the following descriptions of certain embodiments, and will be readily apparent to those skilled in the art having knowledge of various calcium phosphate coating compositions, production techniques and their use in conjunction with implantable medical and dental devices. Such objects, features, benefits and advantages will be apparent from the above as taken into conjunction with the accompanying examples, data and all reasonable inferences to be drawn therefrom, alone or with consideration of the references incorporated herein.

In part, the present invention can be directed to a coating composition, such a composition as can comprise a thermal spraying product of a calcium phosphate particulate component and a biocompatible silicate glass component. Without limitation, such a glass component can comprise about 1 wt. % silica. In certain embodiments, such a silicate glass component can be coupled to at least a portion of the calcium phosphate particulate surface. With respect to either one or a plurality of such particulates, such a silicate glass component can comprise at least about 20 wt. % thereof. Alternatively, from another perspective, at least 20% of the calcium phosphate particulate can have a silicate glass component coupled thereto. In certain other embodiments, such a silicate glass component can be provided as a particulate, and a corresponding coating composition can comprise a thermal spraying product of a physical mixture of calcium phosphate and silicate glass particulates.

Regardless, without limitation, a calcium phosphate component useful in conjunction with the present invention can comprise a calcium phosphate phase selected from various hydroxyapatite phases, various tricalcium phosphate phases and combinations of such phases. In certain such embodiments, such a calcium phosphate component can comprise a biphasic combination of a hydroxyapatite phase and a tricalcium phosphate phase. Regardless, a silicate glass component can comprise less than about 60 wt. % silica. Without limitation as to identity of calcium phosphate and/or silicate glass component, such a composition can optionally comprise a biologically active agent of the sort known in the art, such agents selected from but not limited to bone morphogenetic proteins, platelet-derived growth factors, antibiotics, analgesics and combinations thereof.

In part, the present invention can also be directed to a calcium phosphate bone graft material. Such a material can comprise a particulate thermal spraying product of a calcium phosphate particulate component and a biocompatible silicate glass component comprising less than about 60 wt. % silica, such a particulate product as can be dimensioned from about 50 microns-about 400 microns. Without limitation, such calcium phosphate and silicate glass components can be as mentioned above or described elsewhere herein, and such a material can comprise one or more biologically active agents.

In part, the present invention can also be directed to a calcium phosphate bone graft material not obtained as a thermal spraying product. Rather, such a material can comprise a glass fusion product of a biocompatible silicate glass component fused with and diffused throughout calcium phosphate particulate components. Without limitation, such calcium phosphate and silicate glass component can be as described elsewhere herein. In certain embodiments, such a silicate glass component can be provided as a particulate, such that a physical mixture of particulates can be used to produce a corresponding glass fusion product. In certain such embodiments, such a silicate glass component can comprise about 5 wt. %-about 95 wt. % of such a mixture. Without limitation, about ⅔ of such a mixture can comprise such a calcium phosphate component, whether selected from a hydroxyapatite phase, a tricalcium phosphate phase, combinations thereof, or one or more other calcium phosphate phases known in the art. Regardless, such a material can be utilized as a particulate powder, an aggregate or a molded pre-form in conjunction with a corresponding osteoimplant.

DETAILED DESCRIPTION OF CERTAIN EMBODIMENTS

Certain non-limiting embodiments of this invention can be directed to calcium phosphate powder particles comprising a component and/or surface coating component coupled thereto comprising a silicate content glass; thermal sprayed coatings made from such powder particles, and bone graft materials made from such powder particles. In certain embodiments, the silicate coating can be in the form of a silicate glass material having at least about a 1% silica content. Advantages of the silicate glass component include: 1) a glass coating melts at a lower temperature which helps powder to stick, reducing waste; 2) low melt temperature of the glass component may help to preserve the chemical composition of the coated particles since there is less need to heat the particles above their decomposition point for melting; 3) glass helps to "stick" coating particles together in the coating, increasing strength; 4) glass makes make the coating more biologically active; 5) by contrast, coatings of a pure calcium phosphate glass tend to be too brittle, but ceramic base particles can help reduce brittleness; 6) increased strength of porous particles or blocks; and 7) modification of surface chemistry/charge characteristics for chromatographic purification specificity.

A glass component or coating on the particles can be similar to the well known "Bioglass®" grafting materials. Unlike calcium phosphate ceramics, such bioglass materials have a melting point, and their melting points are many hundreds of degrees lower than the decomposition temperature of calcium phosphates. Therefore, a bioglass type of coating on plasma spray feed particles will enable the particles to become "sticky" at much lower temperatures than uncoated calcium phosphate particles. Because the glass coating melts substantially without decomposition, it can be held in a melted state over a wider range of temperatures without the danger of uncontrolled decomposition that occurs when melting uncoated calcium phosphate particles. This can provide a wider range of coating parameters that still result in a consistent coating. Note that, if desired, the coating can be produced at a high enough temperature to bring about melt-decomposition of the calcium phosphate particles as in a conventional plasma spray coating process. However, with a glass component and/or coating of this invention, melting the calcium phosphate base particles becomes optional, rather than a required part of the coating process. Further, a low melting glass will help to "stick" or adhere the powder particles to the device surface as well as to each other. For a plasma sprayed coating, the presence of the glass helps to ensure more uniform bonding of the coating powder particles because of the greater level of surface melting than would exist without the glass coating being present.

A device or substrate coating made with a glass component or glass-coated particles can have a relatively high silica content. However, it can have areas of high silica content where the glass surfaces between particles have fused together combined with regions of lower, or no silica content, in the regions corresponding to the original particle centers. In cases where the coating particles are small enough that they can be completely melted in the plasma flame, or the temperature is high enough to ensure complete melting of even large coating particles, the composition will be more uniform, and the coating may comprise a relatively uniform calcium phosphate-silica glass phase.

The biological benefits of the coating can be incorporated into materials to be used for bone grafting applications, especially in osseous sites. As detailed, below, such materials can be produced by several methods. One approach is to spray a thick coating on a target plate, then scrape off the coating, grind and sieve it. Another approach is to capture discharged sprayed particles as powder, not a coating. Such powder particles will have a more complete mixing of the glass and calcium phosphate ceramic by virtue of having passed through a high temperature plasma flame.

For the purposes of the present compositions, materials and/or methods, the following expression(s) and words, unless otherwise indicated, will be understood as having the meanings ascribed thereto by those skilled in the art or as otherwise indicated with respect thereto. For instance:

"Biocompatible silicate glass" refers to any biocompatible glass containing silica ($SiO_2$) and comprising compositional features which distinguish such bioactive glasses from traditional inert soda-lime-silicate glasses and provide for bonding and integration with living tissue. Different compositions are possible. Good results are obtainable with a silica content at least about 1%. The most well known compositions are members of the $SiO_2$—$Na_2O$—$CaO$—$P_2O_5$ glass system (U.S. Pat. No. 5,074,916, incorporated herein by reference in its entirety), but any biocompatible glass can be used to provide such a silicate glass component or particle coating. For example, reference is also made to the $Na_2O$—$K_2O$—$MgO$—$Ca$—$B_2O_3$—$P_2O_5$ —$SiO_2$ system (M Brink et. al.; "Compositional Dependence of Bioactivity of Glasses in the System $Na_2O$—$K_2O$ $MgO$—$Ca$—$B_2O_3$ $P_2O_5$ —$SiO_2$"; J Biomed Mater Res 1997; 37:114-121), or any other bioactive glass system known in the art.

"Calcium phosphate" refers to any synthetic or naturally-occurring calcium salt of phosphoric acid with a Ca/P ratio between about 1 and about 2, whether sintered (e.g., at a temperature of about 400° C. or higher) or unsintered. This would include hydroxyapatite, α or β tricalcium phosphate (TCP), biphasic hydroxyapatite/β tricalcium phosphate combinations, pyrophosphate or other calcium phosphates or combinations thereof, such as may have been found useful for bone void fillers, whether fully crystalline or partially crystalline in morphology. Substitutions of different ions within the calcium phosphate system that are known to the art are contemplated. For example, and without limitation, calcium can be substituted in whole or in part with ions such as Mg, Sr, Zn, or other known metal ions; and fluorine, chlorine, carbonate or oxide (e.g., fluoroapatite, chloroapatite, carbonate apatite or oxyapatite) can be substituted for the hydroxide groups in any amount up to and including complete replacement of hydroxide.

A sol-gel process can be used to make the glass covered coating powder. A calcium phosphate powder is first made by conventional manufacturing techniques such as neutralization of a calcium hydroxide slurry with phosphoric acid, or a reaction between calcium nitrate and ammonium phosphate (with added ammonia for pH control). The slurry is preferably spray dried, sintered, and sieved to the final particle size. Alternatively, for example, the material can be oven dried and ground into particles rather than being spray dried. Preferably the material is sintered before being coated. Sintering gives the particles greater stability in the aqueous glass coating solution. The calcium phosphate material is preferably HA, but it can be TCP, a mixture of HA and TCP, or any calcium phosphate (or substituted calcium phosphate) with a Ca/P ratio between about 1 and about 2. After drying, the powder particles can be finished by sieving, tumbling, or any other process known to the art. The glass coating is formed, for example, of a sol-gel slurry of tetraethoxysilane, triethylphosphate, nitric acid and calcium nitrate which is made up, for example, by following the procedures in U.S. Pat. No. 5,074,916 incorporated herein by reference in its entirety. However, rather than carry the process to completion, once the slurry is made, the sintered powder particles are coated with the slurry by any convenient means such as dipping the powder in the slurry, placing the powder on a screen and pouring the slurry over it, etc.

The coated particles are then dried. While air drying is possible, oven drying is preferred (at any temperature up to about 200° C.). Next, (optionally) the dried, coated particles are heated at about 450 to about 800° C. to melt the glass into a coating. The heated particles are cooled, and (optionally) sieved to the final particle size. At least about 5% up to about 90% of the outer particle surfaces must be coated. The particles are then ready for use, although optional additional finishing steps known to the art can be employed first. Such finishing includes sieving to final particle size, and/or any other treatment than may normally be applied to plasma coating powder particles.

An alternative to the sol-gel method is to take a finished glass, grind it to a small particle size (preferably under about 10 microns), mix it with sintered calcium phosphate particles, then sinter the material at a temperature at least equal to the melting temperature of the glass in order to make a melted glass coating on the particles. The glass can be applied to the calcium phosphate particles as a slurry with a bonder such as carboxymethyl cellulose, polyethylene glycol, or any other material know to the art to better hold the glass in place before sintering. It is also possible to supply some type of mixing or tumbling arrangement during sintering (such as a rotary kiln, for example) to facilitate the process of coating the calcium phosphate particles with the glass.

As relates to thermal spray techniques and corresponding thermal spray products, various methods and compositions of this invention can be realized through implementation of a plasma spray system or plasma detonation system. Plasma spray systems are manufactured and marketed under the trade name Metco 7M and Metco 9M 80 kW spray systems. Plasma detonation systems are manufactured and marketed under the trade name Metco Diamond Jet Gun System. The plasma spray system and the plasma detonation system are available from the Metco Division of Sulzer. (A second source of equipment suitable for use with the present invention is Miller Thermal based in Appleton, Wis.) A Metco control unit FMCII and Metco AR2000 6 degree of freedom robot system may be employed to aid in applying the calcium phosphate-containing powder. A Metco 4MP feeder may be employed to deliver the powder to the plasma gun. The foregoing equipment is also available from Sulzer.

Plasma spray systems operate by injecting a calcium phosphate particulate to the inert gas plasma generated by the plasma gun. The plasma gun accelerates the particles to a very high velocity at a very high temperature. The high velocity high temperature plasma spray particulate discharge can be collected or can be directed toward a substrate or target where the particles of the calcium phosphate-containing component strike and coat the target to impregnate (penetrate) the target to form an adherent coating. The adherent coating extends into the preexisting surface pores of the target due to the high discharge velocity. The resulting spray product is understood by those skilled in the art to have material, mechanical and/or chemical properties significantly different from the bulk starting materials. The plasma spray product may be allowed to build up past the surface of the target.

A carrier gas, preferably argon or nitrogen, is required to carry particulates into the electric arc of the plasma gun. The particles of the ceramic material are entrained in a jet of the carrier gas which passes through the electric arc. The power to the electric arc allows differing particle sizes to be used. The gun may also be varied to provide that the particulates strike the substrate/target at a velocity sufficient to cause adherence thereto.

When desired, a plasma detonation system may be employed to deliver to the material to the target. The process in a plasma detonation system is generally similar to the conventional plasma spray process described above. The plasma detonation gun system differs in detonating a mixture of hydrogen and oxygen near the tip of the nozzle through which the calcium phosphate-containing material is fed. The detonation of hydrogen and oxygen in the plasma detonation gun system significantly increases the velocity of the particles in the plasma.

Regardless, the glassy compositions of this invention can be produced by any method that provides extremely rapid heating/melting and cooling. For example, laser melting techniques can be adapted for use in conjunction with this invention, as well as all forms of plasma spraying including flame spraying, wire arc spraying, vacuum plasma spraying, high velocity oxygen fuel (HVOF) spraying, etc. For purposes of this invention, thermal spraying shall be understood as being inclusive of such methods, including plasma spraying, that provide very fast heating (by electrical or chemical means) and cooling. Regardless, as described herein, the calcium phosphate-containing powder can be plasma sprayed onto a substrate/target in accordance with such conventional techniques to provide a coating or layer thereon ranging in thickness from about 0.5 to about 100 microns, preferably from about 10 to about 50 microns. See, for instance, U.S. Pat. No. 6,846,853, the entirety of which is incorporated herein by reference—in particular, example 1 thereof. With a plasma gun running on argon at 300 amps and a feed rate of 20 grams/minute, a composition of this invention can be deposited on a stainless steel substrate, such as a medical implant, at a distance of 70 mm. With sufficient build-up, as discussed below, the resulting composition can be removed, collected and ground to provide a particulate bone grafting material.

Various changes in the plasma coating operating procedures can be made, for instance with use of a coated powder compared to a powder without the glass coating. However, such operating parameter changes are well-known in the art of making plasma sprayed coatings. Non-limiting examples of parameter changes include plasma gun nozzle configuration, plasma gas, plasma gun current, powder feed rate, distance of plasma gun from surface of object being coated, and rate of travel of plasma gun over surface to be coated. While an electrically generated plasma is preferred, a combustion (flame) spray coating process can also be used.

The system of $SiO_2$—$Na_2O$—$CaO$—$P_2O_5$ has been well studied as a tissue grafting material. The best known members of this system are the Bioglass materials, such as Bioglass® 45S5 (with 45% $SiO_2$), or Bioglass® 54S, etc. (See, e.g., the aforementioned, incorporated '916 Patent.) With a $SiO_2$ content below about 60%, these materials show excellent bone bonding. The coated plasma sprayed powder will have a silica content that is somewhat below the silica content of the coating. This is because the melted coating will dissolve some of the calcium phosphate from the particle core which will be incorporated into the glass phase. If some of the calcium phosphate also melts during the plasma spraying process, then the amount of dilution will be greater. However, this still provides a favorable composition for bone bonding as long as the silica content is below about 60%.

The percent of the outer surfaces of the calcium phosphate particles being coated with the glass can vary from about 5% up to 100%. The weight percent of the glass coating compared to the particles can vary from about 1% to about 100%. While the preferred method to make the plasma sprayed coating is to use glass coated powder particles, it is also possible to make the glass containing plasma sprayed coating by spraying a mechanical mixture of calcium phosphate particles and glass particles. The mixture can range from about 5% glass, about 95% calcium phosphate to about 95% glass, about 5% calcium phosphate. The calcium phosphate particles in the feed to the plasma gun can be sintered or unsintered, or a mixture of both.

Alternatively, a glass coating process, such as that described above, can be used to coat calcium phosphate particulates (solid or porous) or calcium phosphate preforms/shapes (solid or porous) and the resulting coated calcium phosphates can be used directly as bone grafting materials, thereby avoiding the plasma sprayed coating step. The particles can be sintered at a minimum temperature (e.g., about 400° C.) to stabilize the coating. Sintering can also be carried out at a higher temperature in order to provide a fusion product of a biocompatible glass with the substrate particles. At a high enough temperature, the glass will fully diffuse throughout the particles such that the composition is substantially uniform, and no longer like a coated material.

Because this material is not plasma sprayed, there are no constraints on physical size and shape that would be needed to put the material through a plasma spray gun. Therefore, it can be in the form of particles of any size, including porous particles and even porous blocks. Such porous materials can be at least about 5% by volume pores, with a minimum size of about 50 microns. Porosity can be up to about 95% with a maximum pore size of up to about 1000 microns.

A bone grafting material, similar in composition to one plasma sprayed coated, can be produced by passing the glass/calcium phosphate feed material through a plasma gun, then collecting the sprayed material. The particle size can be controlled by the size of the plasma feed material; if allowed top cool below the melting point, free particles will be collected that do not fuse together. In one embodiment, the material is collected on a plate, then scraped off and (optionally) ground and sieved to size. The chemical composition of such a material is substantially the same as that of a substrate coating made from the same feed material.

However, depending on the collection conditions, the powder can be substantially different in composition. If sprayed in air, the material will resemble sintered material (even if the calcium phosphate in the feed is unsintered to start). It will also more uniformly incorporate the glass phase as the glass will melt into the calcium phosphate during the high temperature part of the process. The plasma sprayed particles can be recovered dry, but they could also be collected in a container of water, to reduce dusting and better capture the particles.

If sprayed in a dry, oxygen free atmosphere, the collected particles will more closely resemble a substrate-deposited coating in terms of its chemistry. During plasma spraying, calcium phosphates lose some oxygen and water of composition, especially so with HA, which loses hydroxide ions from its calcium hydroxide groups. The resulting free calcium promotes the formation of a glassy network. If the plasma sprayed particles cool in air, they will take up water and oxygen and return to normal. If sprayed on a surface, the rapid quenching can inhibit the uptake of oxygen and water from the air. Likewise, if the particles are sprayed in an atmosphere largely devoid of water and oxygen, they will not be able to fully recover the water and oxygen lost during the plasma spray process.

Regardless, coatings or powders made by the described processes can have one or more therapeutic biologically active agents incorporated therein. Such agents can include, for example, bone morphogenetic proteins and growth factors (such as, e.g., BMP-2, BMP-7, PDGF, etc.), antibiotics, and analgesics known in the art and used in conjunction with compositions of the sort described herein. Single materials or combinations of materials can be added. Addition is preferably by application of a solution of the biological material to the coating or powder with subsequent evaporation of the solvent, but any method known to the art can be used.

EXAMPLES OF THE INVENTION

The following non-limiting examples and data illustrate various aspects and features relating to the compositions, materials and/or methods of the present invention, including the glassy calcium phosphate compositions and related bone graft materials, as are available through the synthetic methodologies described herein. In comparison with the prior art, the present compositions/materials provide results and data which are surprising, unexpected and surprising thereto. While the utility of this invention is illustrated through the use of several compositions/materials and components which can be used in conjunction therewith, it will be understood by those skilled in the art that comparable results are obtainable with various other compositions/materials and calcium phosphate and silicate glass components as are commensurate with the scope of this invention.

Example 1

Preparation of glass-coated particles. Fully sintered (1150° C.) HA particles of a size distribution of 90% from about 5-about 40 microns were obtained. A 45S Bioglass® composition was prepared through the casting stage, but was not dried or sintered. (Reference is made to U.S. Pat. No. 5,147,829—the entirety of which is incorporated herein by reference—and, in particular, the various other biocompatible silicate glass compositions described therein.) The HA particles were submerged into the glass solution, allowed to soak for 10 minutes, then the solution with particles was poured over a 5 micron sieve, allowing the excess glass to drain. The coated particles were collected from the sieve, dried in an oven at 90° C., for 4 hours, then sintered at 600° C. for 3 hours. After sintering, any agglomerates were broken up by passing the plus 50 mesh material through a BICO grinder (equipped with ceramic plates).

Alternatively, such glass-coated particles can be prepared with various other available calcium phosphate components, such as but not limited to α- or β-TCP and/or a combination of an HA and a TCP.

Example 2

Preparation of glass particles. Glass particles (45S2) as described in (M Brink et. al.; "Compositional Dependence of Bioactivity of Glasses in the System $Na_2O$—$K_2O$ MgO—Ca—$B_2O_3$ $P_2O_5$—$SiO_2$"; J Biomed Mater Res 1997; 37:114-121) were prepared following the general procedures in the incorporated U.S. Pat. No. 5,147,829. The finished particles were sieved to a size range of less than 50 microns. Various other bioactive silicate glass components are described in the incorporated '916 and '829 Patents or are otherwise available under the Bioglass® trade name.

Example 3

Preparation of an HA/glass plasma sprayed coating. Materials in accordance with Example 1 can be plasma sprayed on a substrate to make a coating using an electric plasma spray system, such as that manufactured by Miller Thermal. Argon is a recommend gas because it gives a relatively low temperature plasma. The spraying conditions (arc current, powder feed rate, coating distance to the substrate, travers speed, etc.) are chosen to give a surface coating of about 50 microns thickness on a metallic implant such as a hip joint or a dental tooth root implant. After coating, the implant can be cleaned in alcohol, packaged, and sterilized by gamma radiation using procedures known in the art.

Example 4

Preparation of HA/glass plasma sprayed coating from a mixture of HA and glass particles. Calcium phosphate particles in accordance with Example 1 and the glass particles in accordance with Example 2 can be combined in ratio of 2/3 calcium phosphate (e.g., HA) to 1/3 glass (e.g., 45S2) particles. The combination is a physical mixture brought about by, for example, tumbling. The mixed powder/glass particles can be used to produce a coating on an implant, as described in Example 3 and elsewhere herein.

Example 5

Preparation of a bone graft material. The coating described in Examples 3 or 4 can be sprayed on a flat plate to a thickness of several millimeters. This coating can be scraped off of the plate, ground in a BICO gender with alumina grinding plates, and sieved to a particle size of about 50 to about 400 microns. The resulting granulate material (or a molded aggregate or pre-form thereof) is suitable as a bone grafting material for use in conjunction with or as fabricated into an osteoimplant. (See, e.g., the aforementioned incorporated '853 Patent.)

Example 6

Alternate preparation of a bone graft material. HA particles with a size distribution of about 50 to about 400 microns can be produced by the general procedures outlined in Example 1. These can be mixed with the glass particles described in Example 2 (less than about 50 microns) in the 2/3 HA, 1/3 glass ratio as described in Example 5. The resulting mixture can be plasma sprayed in a plasma gun with external feed so that the particles are injected into the plasma flame after the flame has exited the gun nozzle. The plasma flame can be directed into a duct equipped with a high efficiency and an exhaust fan after the filter. The plasma sprayed material can be collected on the filter and recovered by removing it from the filter by shaking or a reverse air flow. The collected material can be processed between 400 micron and 50 micron sieves, with any oversized agglomerates being passed through a BICO mill and re-sieved. The resulting bone graft material provides glass/HA particles with a fairly uniform composition—the plasma spraying process serving to combine the two starting materials.

As would be understood by those skilled in the art in conjunction with the particles of this example and, for instance, the particles of examples 3-5, any calcium phosphate component with a Ca/P ratio of about 1-about 2, or combinations thereof, can be substituted for the HA component used above, such calcium phosphate components include, without limitation, components substituted with various metal cations (e.g., Mg and/or Sr, etc., at least in part for calcium) and/or various anions (e.g., halide or oxide, at least in part for hydroxide).

We claim:

1. A composition comprising a plurality of calcium phosphate particulate components and a biocompatible silicate glass component coupled thereto, said silicate glass component comprising $SiO_2$, CaO and $P_2O_5$, said silicate glass component comprising about 5 wt. % to 33 wt. % silica, said composition comprising said calcium phosphate particulate components with about 5% to about 90% of the surface of said calcium phosphate particulate components coated with said silicate glass component.

2. The composition of claim 1 wherein said silicate glass component comprises at least about 20 wt. % of a said calcium phosphate particulate.

3. The composition of claim 1 wherein at least about 20% of said calcium phosphate particulates have said silicate glass component coupled thereto.

4. The composition of claim 1 wherein said calcium phosphate component comprises a calcium phosphate phase selected from a hydroxyapatite phase, a tricalcium phosphate phase and combinations of said phases.

5. The composition of claim 4 wherein said calcium phosphate component comprises a biphasic combination of about 5 wt.% to about 95 wt. % hydroxyapatite phase and about 95 wt. % to about 5 wt. % of a tricalcium phosphate phase.

6. The composition of claim 1 wherein said plurality of calcium Phosphate particulate components and biocompatible silicate glass component coupled thereto is dimensioned from about 5 microns to about 1000 microns.

7. The composition of claim 1 comprising a biologically active agent selected from bone morphogenic proteins, platelet-derived growth factors, antibiotics, analgesics and combinations of said agents.

* * * * *